United States Patent [19]

Robison

[11] Patent Number: 4,619,935

[45] Date of Patent: Oct. 28, 1986

[54] STABLE ONCOLYTIC FORMULATIONS

[75] Inventor: Robert L. Robison, Greenwood, Ind.

[73] Assignee: Eli Lilly and Company, Indianapolis, Ind.

[21] Appl. No.: 659,389

[22] Filed: Oct. 10, 1984

Related U.S. Application Data

[63] Continuation of Ser. No. 476,077, Mar. 17, 1983, abandoned, which is a continuation-in-part of Ser. No. 399,654, Jul. 19, 1982, abandoned.

[51] Int. Cl.$^4$ ............................................. A61K 31/44
[52] U.S. Cl. .................................................... 514/281
[58] Field of Search .......................... 424/262; 514/281

[56] References Cited

U.S. PATENT DOCUMENTS

| | | | |
|---|---|---|---|
| 3,097,137 | 7/1963 | Beer et al. | 260/244.4 |
| 3,205,220 | 9/1965 | Svoboda et al. | 260/244.4 |
| 3,749,784 | 7/1973 | Johnson | 424/262 |
| 4,188,394 | 2/1980 | Eakins et al. | 424/262 |
| 4,190,673 | 2/1980 | Eakins et al. | 424/324 |
| 4,203,898 | 5/1980 | Cullinan et al. | 424/262 |
| 4,208,414 | 6/1980 | Schinitsky | 424/262 |
| 4,259,242 | 3/1981 | Rolski | 260/244.4 |
| 4,310,528 | 1/1982 | Jovanovics et al. | 424/262 |

FOREIGN PATENT DOCUMENTS 2062464  5/1981  United Kingdom .

OTHER PUBLICATIONS

"Remington's Pharmaceutical Sciences" Mack Publishing Co. (Easton, Pa.) pp. 229–243 (1980).
"Manual of Oncology Therapeutics", The C. V. Mosby Co., Publisher, pp. 212–214 (1981).
Physicians' Desk Reference, 36th Edition (1982), pp. 1129–1130.
Physicians' Desk Reference, 36th Edition (1982), pp. 1142–1144.
APhA Academy of Pharmaceutical Sciences, 129th APhA Annual Meeting, Las Vegas, Nev., 4/24–29/82, vol. 12, No. 1, Abstract No. 15 (Basic Pharmaceuticals Sec., p. 41).
APhA Academy of Pharmaceutical Sciences, 129th APhA Annual Meeting, Las Vegas, Nev., 4/24–29/82, vol. 12, No. 1, Abstract No. 7, (Pharm. Analysis & Control Sec., p. 79).
J. H. Burns in Analytical Profiles of Drug Substances, vol. 1, Academic Press (New York and London, 1972), pp. 463–480.

*Primary Examiner*—Jerome D. Goldberg
*Attorney, Agent, or Firm*—Robert A. Conrad

[57] ABSTRACT

Stable, sterile, ready-to-use formulations of oncolytic vincristine are provided.

8 Claims, No Drawings

STABLE ONCOLYTIC FORMULATIONS

This application is a continuation of application Ser. No. 476,077, filed Mar. 17, 1983, now abandoned, which is a continuation-in-part of Ser. No. 399,654 filed July 19, 1982, now abandoned.

BACKGROUND OF THE INVENTION

The vinca alkaloids are, in general, dimeric indole-dihydroindole compounds. Two of the alkaloids obtained from the leaves of the plant *Vinca rosea*, vincristine (VCR) and vinblastine (VLB), are marketed for the treatment of leukemias and related neoplasms in humans. A third compound, an amide derivative of vinblastine called vindesine (VDS), is marketed for the treatment of neoplastic diseases in humans in several European countries and is on clinical trial in the United States. These three drugs are described in U.S. Pat. Nos. 3,205,220 (vincristine), 3,097,137 (vinblastine), and 4,203,898 (vindesine). The drugs are administered by the intravenous route to patients suffering from susceptible neoplasms. The usual pharmceutical formulation employed has been a lyophilized vial of a sulfate salt which is reconstituted prior to use. The sulfate salts are prepared by adding a theoretical amount of sulfuric acid to a solution of the alkaloidal free base. In the case of vindesine, however, the sulfate made by the ordinary procedure is not stable and a special sulfate disclosed in U.S. Pat. No. 4,259,242 must be employed in the lyophilized pharmaceutical formulation.

It has long been felt desirable to have ready-to-use solutions of vincristine sulfate or other vinca alkaloids for several reasons. In the first place, improper reconstitution of a lyophilized product sometimes results in the formation of air-borne droplets which may be a hazard to the hospital personnel who are making up the solution for an i.v. injection. Vincristine is an extremely potent oncolytic drug and it would seem to be simple common sense to avoid contact with this drug insofar as possible. Furthermore, avoiding all contact with any cytostatic drug and especially vincristine is desirable. In addition, there is always a problem in reconstituting a lyophilized formulation in that an inappropriate quantity of diluent may be used or that an incorrect amount of drug may be used because of a different vial size. The margin between toxic effects and therapeutic dose is relatively small with the vinca alkaloids. Errors in concentration for i.v. injection resulting in accidental overdosages with vincristine have been recorded in the literature. See for example the *Journal of Pediatrics*, 89, 671 (1976), *Cancer Chemotherapy Reports*, 55, 525 (1972), and *Journal of Pediatrics*, 90, 1042 (1977).

Another disadvantage of the lyophilized vincristine sulfate arises from the mode of calculating dose levels for each individual. Vincristine sulfate is supplied in even milligram amounts (e.g., 1 mg. and 5 mg. vials). Since a dose is usually calculated as 2 mg. per square meter of body surface for children and 1.4 mg. per square meter body surface for adults, the doses actually given are usually in decimal milligram amounts, and therefore only part of a vial's contents may be given. In addition, it should be reiterated that there is a narrow margin between the toxic dose and the effective dose of vincristine. Thus, since the dosage is actually calculated in treating humans for leukemias, lymphomas, etc. for which vincristine is recommended as an oncolytic agent, there will ordinarily be some excess of reconstituted vincristine left over after a given treatment. This problem is not particularly serious in a large cancer clinic where there is a daily use of vincristine and what is left over from one patient can be applied to the next. However, the recommended life for reconstituted vincristine is 14 days at refrigerated temperature. Thus, there will be a necessity in many instances for discarding excess reconstituted lyophilized vincristine which has outlived its 14 day dating period. Vincristine is an extremely expensive drug and any amount of it which must be discarded will naturally increase the overall cost of maintaining a cancer clinic.

The physical changes noticed on standing with reconstituted lyophilized vincristine (reconstituted with 0.9% aqueous sodium chloride containing benzyl alcohol as a preservative) are a general haziness of the solution followed by the appearance of a precipitate.

Another problem is the need to incorporate a preservative into any vincristine solution formulation in order to prevent the growth of microorganisms. In general, vincristine solutions cannot be heat sterilized but can be sterilized by filtration. However, even if the latter process is used, a preservative must be present in the diluent used to reconstitute the lyophilized material or in an opened previously sterilized liquid vial because of the possibility of contamination from the air. Otherwise, the excess material would have to be discarded immediately and could not be kept even for the 14 day period discussed above.

Reconstituted solutions of vinblastine sulfate and vindesine sulfate possess similar problems and concerns although because both compounds contain an N-methyl group instead of the more liable N-formyl functionality found in vincristine, the stability problems are less severe as evidenced by a recommended reconstituted stability dating of thirty days.

It is an object of this invention to provide stable, ready-to-use solutions of oncolytic vinca alkaloids for i.v. injection whose use would minimize the contact between hospital personnel and the drug and would provide a single solution strength for all vial and syringe sizes employed thus avoiding error in reconstitution.

SUMMARY OF THE INVENTION

In fulfillment of the above and other objects, this invention provides a stable, ready-to-use, sterile solution of a vinca dimer salt containing in addition a polyol, an acetate buffer system and preservatives.

DETAILED DESCRIPTION AND PREFERRED EMBODIMENT

My novel invention is particularly applicable to the preparation of stable, ready-to-use solutions of vincristine sulfate. It is believed that this invention would also provide stable, ready-to-use solutions of other vinca dimers whose clinical use is not yet certain but which may be put on clinical trial and marketed as oncolytic agents sometime in the future.

Salts other than the sulfate salt, such as the phosphate salt, are utilizable in the stable solutions of this invention although the sulfate salts are preferred. The alkaloids are usually present in the formulation at a concentration of about 0.01 to 2.0 mg./ml., preferably at a concentration of 0.1 to 1.0 mg./ml.

The polyols useful in my novel, stable, ready-to-use solutions of vincristine are generally polyols derived from sugars, such as mannitol and sorbitol, or are sugars themselves such as lactose and sucrose. Other useful polyols will readily suggest themselves to those skilled in the art. Lactose and especially mannitol are the preferred polyols used in this invention. The polyol is usually present in the formulation from about 10–100 mg./ml.

The acetate buffer system utilized in my novel, stable solutions should maintain the pH in the range 3.0–5.0. A pH range of 4.4–4.8 is preferred. I prefer to use a buffer system at a molarity in the range of about 0.02–0.0005M, preferably 0.01–0.002M. The molar ratio of acetate to vinca dimer is preferably about 20 to 1 or less. It is felt that the stabilizing effect of the acetate buffer is in part due to preventing any pH change of the solution due to alkali leaching from the glass or stopper of the vial or from degradation due to the change of pH caused by alkaloid decomposition.

In general, all preservatives tested in solutions of vincristine have had a deleterious effect upon potency, clarity, and pharmaceutical elegance, but, of these, the parabens, methyl and propyl, seem to have little effect on these parameters and are therefore preferred. The parabens may be employed singly or in combination, usually in a total amount of 1–2 mg./ml. Other potential preservatives include benzyl alcohol, phenol, m-cresol, and the like. The liquid formulations produced in this invention are sterilized by filtration.

In addition to the ingredients which are present in my sterile, stable solutions of the alkaloids, it is important that the chloride ion concentration be minimized since I have found that chloride ion has a deleterious effect on the various oncolytic vinca dimers, stable solutions of which are provided by this invention.

An example of a stable, ready-to-use solution of vincristine sulfate is as follows: a 1 mg. vial contains vincristine sulfate, 1 mg.; methyl paraben, 1.3 mg.; propyl paraben, 0.2 mg.; mannitol, 100 mg.; acetic acid, 0.0255 ml. of a 0.2M solution; sodium acetate, 0.0245 ml. of a 0.2M solution; water q.s. to 1 ml. Vials containing 2 mg. or 5 mg. of drug are prepared in similar fashion with proportionately larger amounts of materials. The solution thus prepared is sterile filtered and introduced into compatible glass vials in the proper volume. The vials are usually purged with an inert gas, such as nitrogen, before the vials are sealed with a compatible stopper.

Alternatively, the sterile filtered solution may be filled into hypodermic syringes of pre-determined volume to provide a ready-to-use solution which is also ready to inject. Use of the pre-filled syringe further reduces the chance of exposure to patients or hospital or pharmacy personnel by eliminating the need to transfer the vial's contents to an empty syringe. Ideally, the syringe should be graduated and disposable.

Ready-to-use formulations of this type must be stable for periods allowing for distribution to the pharmacy and a reasonable shelf life. Accordingly, vincristine sulfate formulations prepared according to this invention have remained physically and chemically acceptable for pharmaceutical use for periods up to one year at 5° C.

The formulations of this invention were evaluated as to their stability by using analytical high pressure liquid chromatography and thin layer chromatography to ascertain vincristine content and quality. For example, three lots of formulated vincristine sulfate maintained 94–99% of their initial concentration after storage at 5° C. for about nine months. These three lots had the following composition: Vincristine sulfate, 1 mg./ml. of solution; methyl paraben, 1.3 mg./ml. of solution; propyl paraben, 0.2 mg./ml. of solution; mannitol, 100 mg./ml. of solution; acetic acid, 0.0255 ml. of a 0.2M solution per ml. of solution; sodium acetate, 0.0245 ml. of a 0.2M solution per ml. of solution; water, to volume. The solutions were sterile filtered and placed in amber type 1 acid treated vials which were then capped with Teflon-faced gray-butyl stoppers or Stelmi 632 stoppers. (Teflon is the registered trademark of E. I. duPont de Nemours & Co., Inc. for polytetrafluoroethylene resins and products.) The final pH of the solution was approximately 4.6.

I claim:

1. A formulation comprising a stable, sterile, ready-to-use solution suitable for i.v. injection containing about 1–2 mg./ml. of a salt of vincristine, about 10–100 mg./ml. of a polyol selected from the group consisting of mannitol, sorbitol, and sucrose, an acetate buffer in the range of about 0.02–0.0005M to maintain the pH of the solution between 3.0 and 5.0, about 1–2 mg./ml. of a preservative selected from the group consisting of methyl paraben and propyl paraben, singly or in combination, and water.

2. A formulation according to claim 1 substantially free of chloride ion.

3. A formulation according to claim 1 in which the polyol is mannitol.

4. A formulation according to claim 1 in which the concentration of the acetate buffer is 0.01–0.002M.

5. A formulation according to claim 1 containing per ml. of final solution about 1 mg. of vincristine sulfate, 10–100 mg. of mannitol, 1–2 mg. of a preservative selected from the group consisting of methyl paraben and propyl paraben, singly or in combination, and water q.s. to 1 ml., with the pH of said solution being maintained by a 0.02–0.0005M acetate buffer.

6. A formulation according to claim 5 in which the buffered pH range is 4.4–4.8.

7. A formulation according to claim 6 in which the concentration of the acetate buffer is 0.01–0.002M.

8. A formulation according to claim 7 which contains, per ml. of final solution, about 1 mg. of vincristine sulfate, 100 mg. of mannitol, 1.3 mg. of methyl paraben, and 0.2 mg. of propyl paraben.

* * * * *